United States Patent
Neuenfeldt et al.

[11] Patent Number: 5,964,261
[45] Date of Patent: Oct. 12, 1999

[54] IMPLANTATION ASSEMBLY

[75] Inventors: Steven Neuenfeldt, Vernon Hills; Joanne Daugird, Ingleside, both of Ill.; James Brauker, Flagstaff, Ariz.; Robin Lee Geller, Buffalo Grove, Ill.; Scott Fredericksen, Kenosha, Wis.; Mark Jones, Mudelein; Thomas Loudovaris, Grayslake, both of Ill.; David Maryanov, Kenosha, Wis.; Stephanie Shors, St. Charles, Mo.

[73] Assignee: Baxter International Inc., Round Lake, Ill.

[21] Appl. No.: 08/864,209

[22] Filed: May 28, 1997

Related U.S. Application Data

[63] Continuation-in-part of application No. 08/654,729, May 29, 1996, abandoned.

[51] Int. Cl.⁶ .............................. A61F 2/02; A61L 27/00; A61M 31/00
[52] U.S. Cl. ...................... 141/327; 141/100; 141/313; 141/325; 141/329; 206/439; 424/424
[58] Field of Search .............................. 141/2, 9, 10, 18, 141/100, 313, 325–327, 329; 424/424; 206/438, 439

[56] References Cited

U.S. PATENT DOCUMENTS

| | | |
|---|---|---|
| Re. 31,135 | 2/1983 | Winchell et al. . |
| 3,625,786 | 12/1971 | Pearson et al. ............................ 53/289 |
| 3,894,538 | 7/1975 | Richter .................................... 424/424 |
| 4,140,162 | 2/1979 | Gajewski et al. . |
| 4,181,140 | 1/1980 | Bayham et al. . |
| 4,267,269 | 5/1981 | Grode et al. . |
| 4,294,247 | 10/1981 | Carter et al. . |
| 4,294,891 | 10/1981 | Yao et al. ................................... 429/2 |
| 4,298,002 | 11/1981 | Ronel et al. . |
| 4,327,726 | 5/1982 | Kwong et al. . |
| 4,402,682 | 9/1983 | Garver, Sr. et al. . |
| 4,413,992 | 11/1983 | Soika . |
| 4,508,534 | 4/1985 | Garver, Sr. et al. . |

(List continued on next page.)

FOREIGN PATENT DOCUMENTS

| | | |
|---|---|---|
| 0 075 762 | 4/1983 | European Pat. Off. . |
| 0 233 763 | 5/1987 | European Pat. Off. . |
| A 0 359 575 | 3/1990 | European Pat. Off. . |
| WO 93/21902 | 11/1993 | WIPO . |
| WO 93/16685 | 9/1995 | WIPO . |
| WO 96/01611 | 1/1996 | WIPO . |

OTHER PUBLICATIONS

Freshney, R.I., "Disaggregation of the Tissue and Primary Culture," *Culture of Animal Cells: A Manual of Basic Technique,* Chapter 11, pp. 99–118, New York: Alan R. Liss, Inc., (1983).

Geller, R.L., et al., "Immunoisolation of Tumor Cells; Generation of Antitumor Immunity Through Indirect Presentation of Antigen," *Journal of Immunotherapy,* vol. 20, No. 2, pp. 131–137 (1997).

(List continued on next page.)

[57] ABSTRACT

An implant assembly and methods for loading implant devices which avoids the accidental deposition of transplanted material or other contaminates on the exterior of the device during transportation, storage, and handling are disclosed. The implant assembly of the invention may be used with a large variety of implant devices for implanting a variety of materials such as cells, tissue or other materials into a host. The implant assembly includes an implant device having an elongated port and a first chamber for holding material for implantation and a container with a second chamber for holding the implant device. The container functions to maintain the sterility and protect the physical integrity of the implant device during loading, storage, cryopreservation and transportation and is removed immediately prior to implantation of the device. The container may optionally include liquid media for cellular growth, maintenance, cryostorage, or transportation purposes.

25 Claims, 10 Drawing Sheets

U.S. PATENT DOCUMENTS

| | | | |
|---|---|---|---|
| 4,511,355 | 4/1985 | Franetzki et al. | 424/424 |
| 4,574,456 | 3/1986 | Soika . | |
| 4,588,085 | 5/1986 | Sussman | 206/438 |
| 4,710,532 | 12/1987 | Hull et al. . | |
| 4,711,922 | 12/1987 | Hull et al. . | |
| 4,712,681 | 12/1987 | Branemark et al. | 206/438 |
| 4,726,404 | 2/1988 | Haber et al. | 141/59 |
| 4,748,124 | 5/1988 | Vogler . | |
| 5,071,760 | 12/1991 | Watanabe et al. . | |
| 5,314,471 | 5/1994 | Brauker et al. . | |
| 5,344,454 | 9/1994 | Clarke et al. . | |
| 5,418,154 | 5/1995 | Aebischer et al. | 435/182 |
| 5,453,278 | 9/1995 | Chan et al. . | |
| 5,593,440 | 1/1997 | Brauker et al. . | |
| 5,614,205 | 3/1997 | Usawa . | |
| 5,630,843 | 5/1997 | Rosenberg . | |
| 5,653,688 | 8/1997 | Mills et al. | 604/57 |
| 5,868,244 | 2/1999 | Ivanov et al. | 206/63.3 |

OTHER PUBLICATIONS

Y. Nakamura, et al., "A New Compact and Cell Dense Continuous Culture System," *Journal of Immunological Methods,* vol. 118, pp. 31–35 (1989).

Derwent Abstract, WO 9636694 A.

Derwent Abstract, US 5,560,956 A.

Derwent Abstract, US 5,427,742 A.

Derwent Abstract, US 5,354,370 A.

Derwent Abstract, GB 2091853.

Derwent Abstract, SU 294611 A.

Bergers, et al., Interleukin–2 Containing Liposomes, Pharmaceutical Research, vol. 10, No. 112, pp. 1715–1721 (1993).

Carr–Brendel, et al., J. Cellular Biochem. 18A, p. 223 (1994).

Freshney, Culture of Animal Cells, A Manual of Basic Technique, Chapter 18, pp. 189–198 (1983).

Sharp, D. W., MD., "Isolation and Transplantation of Islet Tissue," *World J. Surg.* vol. 8, pp. 143–151 (1984).

*Primary Examiner*—J. Casimer Jacyna
*Attorney, Agent, or Firm*—McDonnell, Boehnen, Hulbert & Berghoff

IMPLANTATION ASSEMBLY

CROSS-REFERENCE

This application is a continuation-in-part of U.S. application Ser. No. 08/654,729, filed May 29, 1996, which is incorporated by reference in its entirety, now abandoned.

FIELD OF THE INVENTION

The present invention relates to a system and method for implanting devices into mammals. In particular, the present invention relates to a container for preventing contamination of implant devices during handling prior to implantation.

BACKGROUND OF THE INVENTION

Implant devices for holding cells or tissue which secrete therapeutically useful substances are useful in a number of medical applications which include treatment of diabetes and gene therapy for treating cancer. Generally, the implant devices are manually loaded with cells or tissues and stored in saline or growth medium prior to implantation. At any point during the handling process, the exterior surface of the implant device may become accidentally contaminated with transplanted cells, tissues, or other materials. Contamination of an implant device may result from spillage of cell suspensions, handling the device with contaminated gloves or instruments, and leakage due to mechanical damage of the device. The presence of contaminating cells, especially transformed cells used in gene therapy applications, may function as sites for tumor growth. Accordingly, there is a need in the art for a method and apparatus which protect implant devices from accidental contamination of exterior surfaces and from mechanical damage during loading, storage, transportation and implantation.

SUMMARY OF THE INVENTION

The present invention relates to an implant assembly and methods for loading implant devices with cells, tissues and other materials which avoids the accidental deposition of transplanted material or other contaminants on the exterior of the device during handling. The implant assembly of the invention may be used with a large variety of implant devices for implanting cells, tissue or other materials into a host.

One objective of the invention is to provide an implant assembly which comprises an implant device comprising porous walls defining a first chamber having an elongated port means providing access to the first chamber; and a container defining a second chamber. The container functions to maintain the sterility and protect the physical integrity of the implant device during loading, storage, cryopreservation and transportation and is removed immediately prior to implantation of the device.

The implant device is within the second chamber and the container has a means for admitting liquids into the second chamber. The elongated port means of the implant device extends from the first chamber through the container. The exterior of the port means forms a seal with the container. If desired, the elongated port means may be in communication with a multiple access means.

Another objective of the invention is to provide an implant assembly wherein the second chamber contains liquid media for cellular growth, maintenance, cryostorage, or transportation purposes. Both the means for introducing liquid and the access means of the multiple access means are closed and the implant device is sealed in a closed sterile system and is ready to accommodate cells, tissues, or other materials for implantation.

A further objective of the invention is to provide an implant assembly wherein the first chamber contains cells, tissue or other materials to be implanted and the second chamber contains liquid and the interior of the elongated port is sealed. In this embodiment, materials to be implanted are introduced into the implant device via the elongated port in communication with tissue transfer instruments. After loading the device, the elongated port is sealed, e.g., with an adhesive using a port sealing instrument connected to the port tube. The implant assembly containing cells or tissue and fluid may be stored in an incubator for culturing purposes, transported for immediate use, or cryopreserved at subzero temperatures until needed.

The entire implant assembly may be optionally enclosed in an pouch to protect and reduce possible contamination of the device and container. If desired, multiple implants devices could be placed in the pouch and sterilized.

Other objectives of the invention include methods for manufacturing, methods for loading, and methods for using such implant assemblies and devices.

These and other objectives and benefits of the invention will become apparent in light of the detailed description below.

DESCRIPTION OF THE DRAWINGS

FIG. 3 shows the device of FIG. 2 rotated 90° so that liquid can be introduced into chamber 6 through access means 7.

FIG. 4 illustrates the assembly of FIG. 3 with closures 13, 14 and 15. Syringe 20 is filled with sealant 23 in barrel 22.

DETAILED DESCRIPTION OF THE INVENTION

The present invention relates to an implant assembly and methods for loading implant devices with cells and tissues which prevents deposition of transplanted cells, tissues, or other contaminants on the exterior of the device.

The implant assembly of the invention reduces airborne or contact contamination of the exterior of the implant device that might result from handling, loading, or sealing the device prior to implantation. Sterilization of the exterior surface of the assembly following tissue loading further reduces the risk of contamination prior to implantation. The implant assembly accommodates a large variety of ported implant devices for implant cells or tissue, provides superior loading and distribution of materials such as cells or tissue within the devices, as well as providing a suitable environment for the cells or tissues until implantation. Loaded implant assemblies may be supercooled for cryopreservation of the loaded materials. The implant assembly is illustrated in FIGS. 1 through 5.

Figure 1:
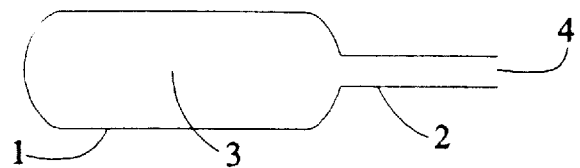
FIG. 1 provides a plane view of an implant device 1 with an elongated port 2 and a chamber 3 for receiving material to be implanted through the elongated port opening 4.

In one embodiment of the invention, an implant assembly is provided which comprises an implant device having an elongated port and a container having a chamber for holding the implant device. FIG. 1 illustrates an implant device 1 with an elongated port 2 and a chamber 3 for receiving material to be implanted through the elongated port opening 4.

A wide variety of ported implant devices can be used in the implant assembly of the invention. See, for example, Taiariol, et al., U.S. Pat. No. 5,017,490 and others drawn to ported implant devices. U.S. Pat. Nos. 5,432,278; 5,314,471 and 5,344,454 and PCT/US95/08151, incorporated by reference in their entirety, describe suitable implant devices for use in the present invention. The preferred implant device, described in the co-pending application Ser. No. 8/179,860 filed Jan. 11, 1994 and co-pending application Ser. No. 8/210,068 filed Mar. 17, 1994, prevents direct cell-to-cell contact between the cells of a host's immune system and the cells in the implant device. This device is comprised of two bilayer membranes surrounded by a polyester mesh sonically welded together, with a port for access to the lumen. Each bilayer comprises a 5 μm polytetrafluoroethylene (PTFE) membrane manufactured by Gore, Flagstaff, Ariz., Product No. L31324 and a 0.45 μm PTFE membrane manufactured by Millipore, Bedford, Mass., Product No. SF 1R848E1. At one end there is an elongated polyester (PE100 ID 0.034" by OD 0.050", Becton-Dickenson) port to permit access to the interior of the device for loading cells. Previous studies have shown that this preferred device has the advantage (though not required for all embodiments of the present invention) of being able to protect allograft tissue from immune rejection for extended periods (Carr-Brendel, et al., *J. Cellular Biochem.*, Vol. 18A, p. 223 (1994) and Johnson, et al. *Cell Transplantation J.*, p. 220 (1994)).

Figure 2:
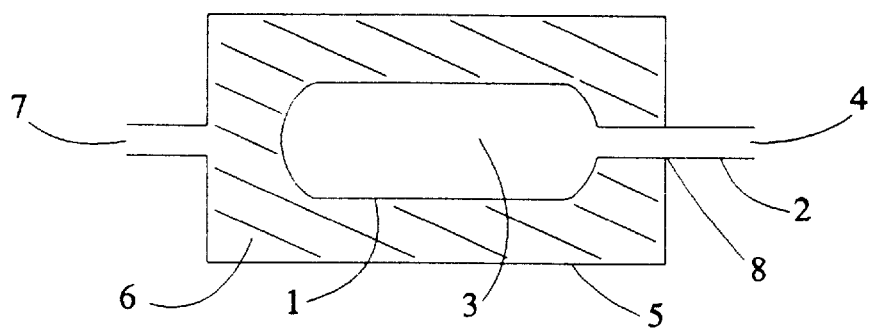
FIG. 2 provides a plane view illustrating the implant device 1 in chamber 6 of container 5.

FIG. 2 illustrates the implant device 1 in chamber 6 of container 5. Container 5 has an access means such as a pocket, portal, injection site or port 7 for introducing liquid into chamber 6. The elongated port 2 of the implant device 1 protrudes through the container 5 and there is a seal 8 between the exterior of the elongated port and the opening in the container where they meet.

The choice of container materials is dependent on the desired properties and the ability of such materials to bond to the implant device port material. Container material properties to be considered include, but are not limited to, clarity, ductility, gas barrier properties, mechanical strength, dimensional stability, residual leaching capability, biocompatibility, usable temperature range, and seal processabilty, by either ultrasonics, heat or radio frequency sealing. Suitable container materials include hydrocarbon plastics and elastomers, such as polyolefins (polyethylene, polypropylene), natural rubber or synthetic elastomers; carbon-chain polymers, such as polystyrene, acrylic, polyvinyl esters (polyvinyl alcohol, polyvinyl acetal, ethylene vinyl acetate copolymer); heterochain thermoplastics, such as polyamides, polyester, polyether and cellulosic polymers; and thermosetting resins, such as phenolic, amino, unsaturated polyester, epoxy, polyurethane and silicone. In practicing the invention, the container is readily transparent for ease in observing and handing the implant device during loading.

The container can be formed in various ways depending on the container material selected. Forming the container can be accomplished by sealing the side seals of container 5 using ultrasonic welding, heat sealing, radio frequency sealing and solvent/adhesive bonding. The preferred method for forming side seals of the container is with ultrasonic welding.

Once the assembly is formed with the implant device inside the container, the entire assembly may be packaged in a removable overpouch and sterilized using ethylene oxide gas (ETO), or other suitable sterilization technique.

Other suitable overpouch materials include hydrocarbon plastics, such as, polyolefins (polyethylene, polypropylene, carbon-chain polymers, heterochain thermoplastics, and thermosetting resins in combination with a nonwoven plastic or surgical grade paper. A preferred overpouch is a Dual Peel Pouch® (Baxter Healthcare Corporation) made of Tyvek® materials available from I.E. duPont and polyethylene. In practicing the invention, the overpouch will use a clear plastic (e.g. polyethylene) face for visual presentation and plastic venting material like Tyvek® for aeration. The overpouch preferably has means for removing the implant assembly such as a ziplock, tearoff or peel strips.

In this embodiment of the invention, the implant assembly can be shipped dry to a surgical site for subsequent loading and sterilization. At the surgical site, the overpouch is removed and the implant assembly is prepared for loading by wetting the implant assembly, introducing liquid media, e.g., saline, into the container via the access means before sealing the container, and priming the implant device to remove air bubbles prior to loading. A procedure for preparing the implant assembly is provided in Example 1 below.

In another embodiment of the invention, a sterile implant assembly is prepared which includes a sealed container having liquid, e.g., saline or growth media, and a pre-wetted and primed implant device ready for loading. The pre-filled implant assembly is overpouched. Example 2 describes a procedure for filling and sealing containers holding implant devices and for wetting and priming the implant devices.

Figure 3:
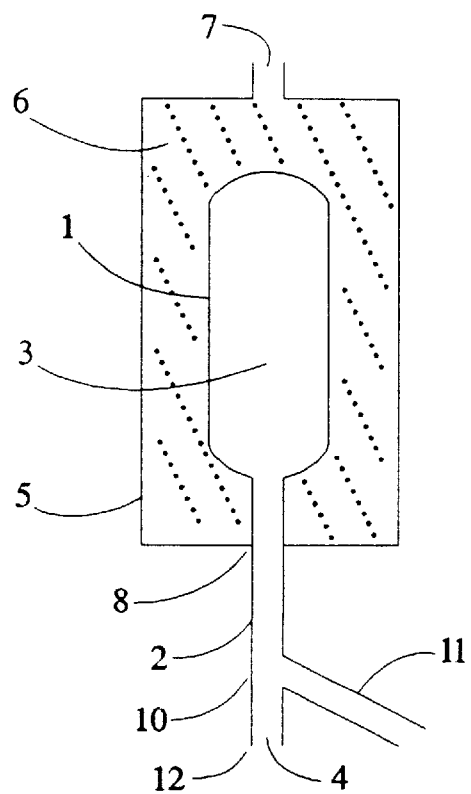
FIG. 3 provides a plane view of the implant assembly of FIG. 2 with an implant device having an elonged port with multiple port openings.

FIG. 3 shows the implant device of FIG. 2 rotated 90° so that liquid can be introduced into chamber 6 through access means 7 to wet the implant device 1 with a wetting solution such as alcohol and to rinse chamber 6 with a liquid, e.g., saline. A 95% aqueous ethanol solution is suitable for wetting. The elongated port 2 is fitted with a conduit 10 which provides communication with multiple ports 11 and 12 into chamber 3 by way of the elongated port opening 4. Chamber 6 is filled with the solution and any air is primed out of chamber 6 by, for example, pressing on container 5. Any air is removed from chamber 3 by pressing through container 5 against device 1 and working the air out through port 2 and conduit 10. Port 7 is closed by, for example, capping, plugging, or sealing with heat, sealant, or adhesive. Ports 11 and 12 are closed by, for example, capping or injecting a silastic sealant.

Any suitable liquid which maintains viability (if cells are used) or stability of the implantable material may be used to fill the container. The c (ell type or properties of the materials to be implanted determines the type of media used. Moreover, the purpose of the liquid determines the type of solutions that may be used, e.g., maintaining, storing, transporting or promoting cell growth. For cells, suitable media include, without limitation, cell specific growth media, PBS, Plasmalyte® and non-buffered saline. Saline is suitable for implantation of drugs or drug formulations. For cryopreservation purposes, suitable media include Dulbecco's modified eagles medium (DMEM)(Irvine Scientific, Santa Ana, Calif.); Fetal bovine serum (FBS) (Harlan Bioproducts, Indianapolis, Ind.); Human Serum; Dimethyl Sulfozide (DMSO)(Sigma Chemical Company, St. Louis, Mo.); and Glycerol (Sigma Chemical Company, St. Louis, Mo.; this may be an alternative to DMSO).

A preferred freezing solution consists of 45% DMEM, 40% FBS, and 15% DMSO. Preservation procedures are generally described in R. Iam Freshney, "CULTURE OF ANIMAL CELLS: A Manual of Basic Technique"; Alan R. Liss Publishing, Inc., New York, which is incorporated by reference in its entirety.

Figure 10:
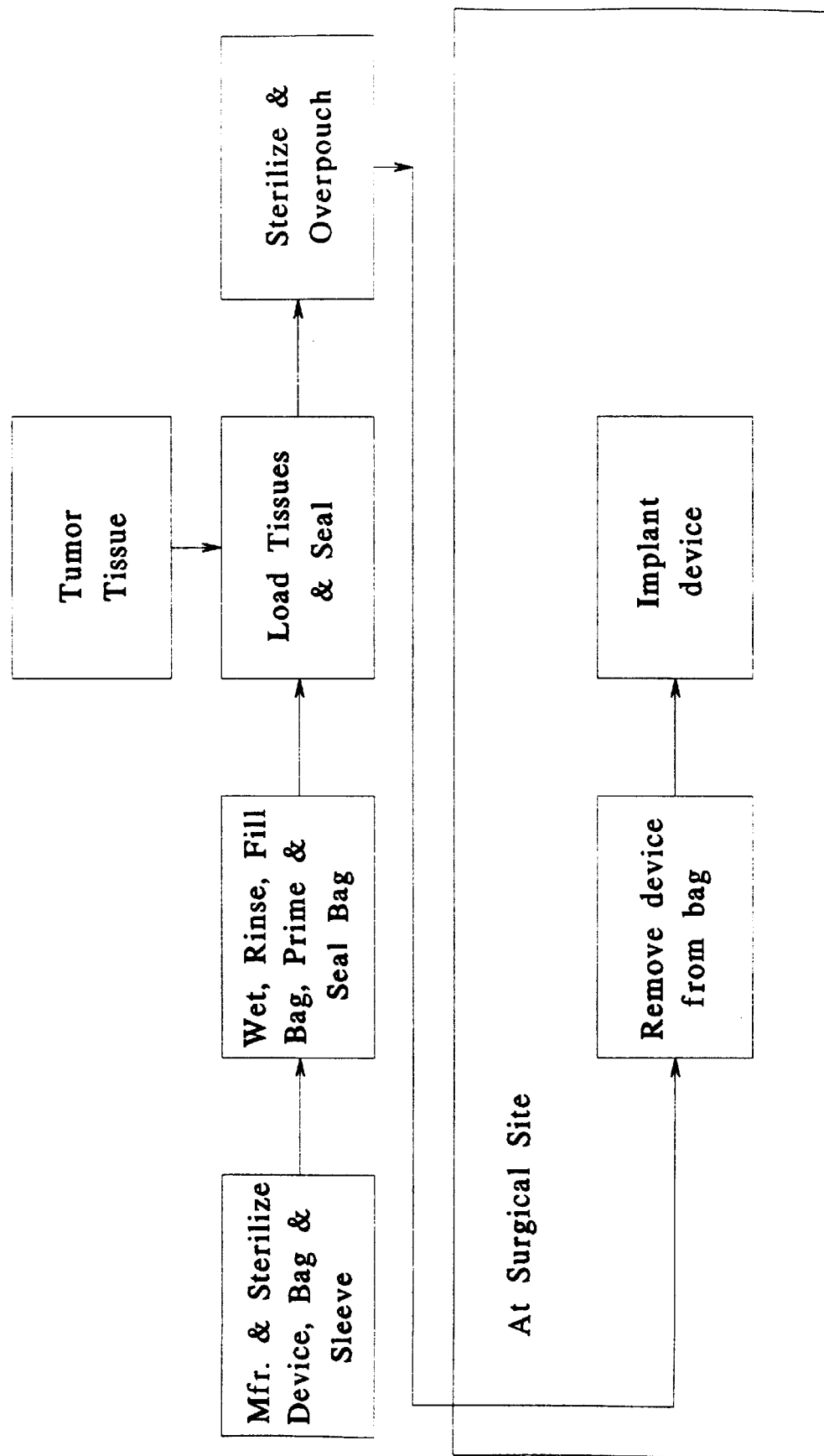
FIG. 10 is a schematic illustrating the process for manufacturing and shipping a ready-to-use implant assembly which is pre-filled with sterile media and pre-loaded with allograft cells. Example 3 provides a suitable procedures for preparing the pre-loaded implant assembly.

In another embodiment of the invention, a ready-to-use implant assembly is provided which is pre-filled with liquid media and pre-loaded with allograft cells or other implantable materials. The entire implant assembly is prepackaged in a sterile overpouch and shipped to the surgical site for immediate implantation or cryoperserved for future use. Example 3 provides a suitable procedure for preparing the pre-loaded implant assembly. FIG. 10 is a schematic illustrating the process for manufacturing and shipping a ready-to-use implant assembly which is pre-filled with sterile media and pre-loaded with allograft cells.

Figure 4A:
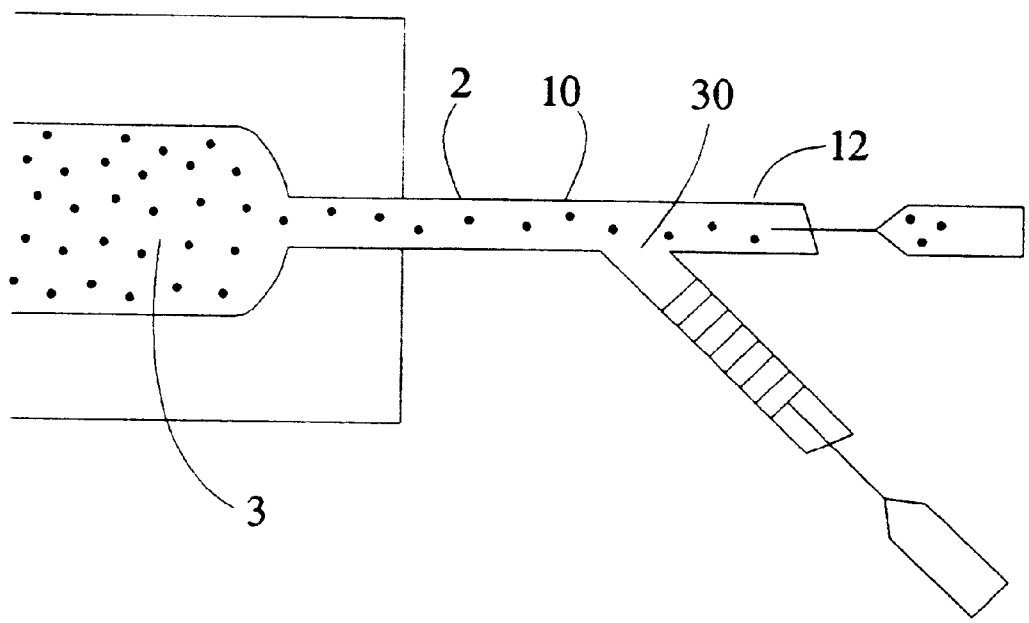
FIG. 4(a) provides a plane view of implant assembly prior to the introduction of material and sealant.
Figure 4B:
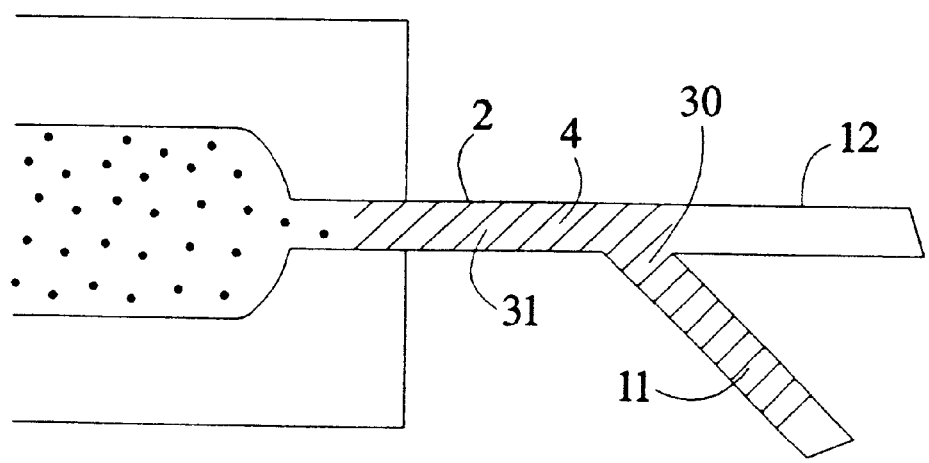
FIG. 4(b) illustrates materials such as cells or tissue flowing 30 from port 12 through conduit 10 and through the elongated port 2 into chamber 3.
Figure 4C:
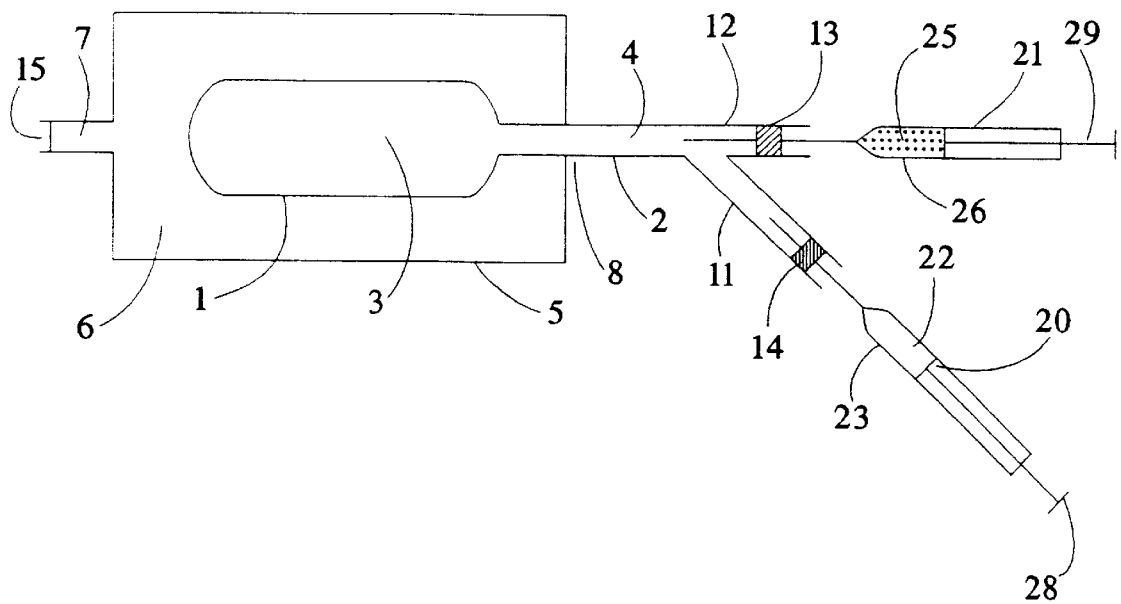
FIG. 4(c) illustrates sealant 31 flowing from port 11 through conduit 10 to seal or plug the interior 4 of elongated port 2. Once the sealant is in place, it can be cured at ambient temperatures.

FIG. 4 illustrates the loading setup and the assembly of FIG. 3 with closures 13, 14 and 15. Syringe 20 is filled with sealant 22 in barrel 23. Syringe 21 is fitted with material to be implanted 25 in barrel 26. Thus, materials to implanted 25, such as liposomes or cells or tissue can be effectively introduced into chamber 3 of the implant device 1 by pushing plunger 29. Hamilton syringes with appropriate needles can be used for introduction of materials. When the desired amount of material is introduced into chamber 3, sealant from syringe 23 can be introduced by pushing plunger 28 until the elongated port is filled with sealant. If sealant is introduced prior to removing syringe 21 from port 12, then backflow of materials from chamber 3 is avoided.

A wide variety of materials can be loaded into the implant assembly of the invention. Suitable materials include, without limitation, cells and tissue derived from autologous, xenograft, or allograft sources, drug-containing liposomes, and time release drug formulations. Other device materials suitable for implantation include sensors, inert materials for reconstruction surgery, catheters for peritoneal dialysis or other implant materials requiring the prevention of fibrotic tissue. Example 3 describes a procedure for loading materials into an implant assembly.

Liposomes for use in the implant assembly are available from a number of sources including Oncotherapeutics, Inc. (Cranbury, N.J.), Liposome Technology, Inc. (Menlo Park, Calif.), The Liposome Company (Princeton, N.J.) and Vestar, Inc. (San Dimas, Calif.). Methods for making and using liposomes are known in the art. See, eg. Bergers, et al., Interleukin-2 Containing Liposomes, *Pharmaceutical Research*, Vol. 10, no. 12, pp 1715–1721 (1993); Sencer, et al., Antitumor Vaccine Adjuvant Effects on IL-2 Liposomes, *Eur. Cytokine Net.*, Vol. 2, no. 5, pp. 311–318, (1991).

FIG. 4a illustrates materials such as cells or tissue flowing 30 from port 12 through conduit 10 and through the elongated port 4 into chamber 3. FIG. 4b further illustrates sealant 31 flowing from port 11 through conduit 10 to seal or plug the interior 4 of elongated port 2 after materials have been loaded into the implant device. Once the sealant is in place, it can be cured at ambient temperatures.

Sealants may be selected from a variety of materials such as silicone curing systems, polyurethanes, and cyanoacrylates. A preferred sealant is moisture cure Type silicone, as sold by Dow Coming. Other suitable sealants include two part elastomers, two part polyurethanes, cyanoacrylate and two part epoxies.

Since visible inspection and detection of loaded materials and sealants can be important for control of quality, dyes or stains which aid in observation of the sealants are desirable. Selection criteria for colorants include biocompatibility and visibility. Colorants can be selected from phenol red, M.A. Hanna Color Blue, M.A. Hanna Color Red, and crystal violet. A preferred dye is M.H. Hanna Color Red.

Figure 5:
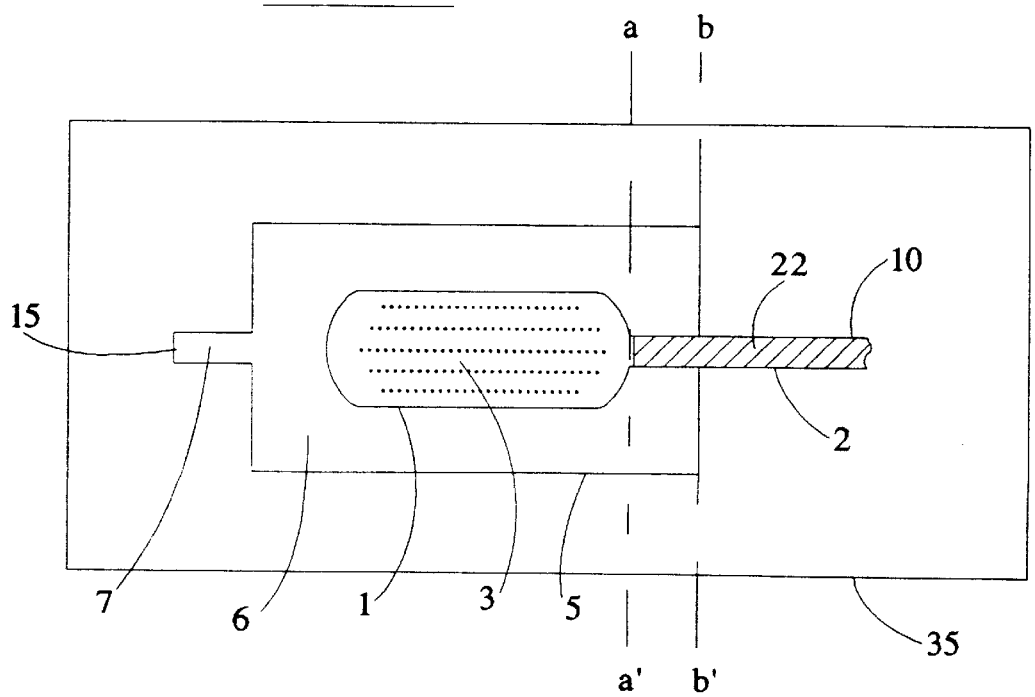
FIG. 5 provides plane view of implant assembly where the elongated port 2 is filled with sealant 22 and severed from 10 by cutting. The implant assembly may be enclosed in a sterile pouch 35. Container 5 may be sterilized prior to or after being placed in the pouch 35.

FIG. 5 illustrates the implant assembly comprising an implant device I in a bag container 5 wherein the elongated port 2 is filled with sealant 22 and severed from 10 by cutting. The implant assembly may be enclosed in a sterile overpouch 35. Container 5 may be sterilized prior to or after being placed in the overpouch 35. The container may be removed from the overpouch by peeling. The implant device 1 can then be removed from container 5 for implantation by cutting the container along line aa'. The overpouch is preferably a Dual Peel Pouch® (Baxter Healthcare Corporation) made of Tyvek® material available from I.E. duPont, but other suitable materials can be selected from hydrocarbon plastics and elastomers, such as polyolefins (polyethylene, polypropylene), natural rubber or synthetic elastomers; carbon-chain polymers, such as polystyrene, acrylic, polyvinyl esters (polyvinyl alcohol, polyvinyl acetal, ethylene vinyl acetate copolymer); heterochain thermoplastics, such as polyamides, polyester, polyether and cellulosic polymers; and thermosetting resins, such as phenolic, amino, unsaturated polyester, epoxy, polyurethane and silicone. The pouch can be constructed such that it can be peeled to open so that the device may be removed.

At the time of implant, the elongated port filled with cured sealant may be severed from container 5, and conduit 10 by cutting along line a–a', releasing implant device 1 from container 5 and releasing the solution from the container. Alternatively, if the device loaded with material is to remain in container 5 for a period of time to permit storage or shipping, then the elongated port 2 may be severed from the assembly along line b–b', thereby retaining the implant device and the solution in container 5.

Colorant may be added to the material, cells or tissue which are loaded into the implant device. This colorant is instrumental in determining the progress of loading of material, cells or tissue into the implant device. A preferred colorant is M.A. Hanna Color Red.

The implant assembly of the present invention can be preserved cryogenically. Freezing the loaded assemblies containing live cells can be accomplished by adding a preservative such as dimethyl sulfoxide (DMSO) or glycerol to the media in the container and then supercooling the assembly. The assembly can be stored for long periods of time (several years or more) preferably below –70° C. in liquid nitrogen. Upon thawing and implantation the assembly still contains viable cells. Cryopreservation of cells is generally known in the art, see, for example Freshney, "Culture of Animal Cells, A Manual of Basic Technique," ch. 18, p.191 (1983). Example 4 provides a suitable procedure for cryogenic storage of implant assemblies containing cells.

There are a number of advantages that can be obtained from using the assembly of the invention. First, isolating an implant device within the container will substantially reduce the risk of airborne or contact contamination of the implant device before, during and following tissue transfer or sealing procedures. The exterior surface of the container following tissue loading may be readily sterilized and this will further reduce the contamination risk prior to implantation.

Second, the configuration of the assembly allows for relative ease in instilling cells and tissues into the implant device without the risk of contaminating the exterior surfaces of the implant device with transplanted cells, tissues or other contaminants. Cell viability is maintained during and following loading due to the fluid in the container. The assembly could be supplied sterile, wetted, air free and ready for connection to tissue transfer and sealing instruments.

Third, the ability to store media for growth, maintenance and other purposes within the assembly can substantially enhance cell and tissue viability before implantation. Cells and tissue stored in the assembly can be cryopreserved and thawed when needed.

Fourth, the assembly can be sterilized by conventional means and overpouched to insure sterility and facilitate storage of the implant device before loading. Multiple implant devices and bags could be overpouched and sterilized. Physical damage to the implant device would further be minimized due to the protection of the container and surrounding media.

The following Examples describe procedures for preparing an implant assembly without cells or media (Example 1), with media alone (Example 2), with media and cells (Example 3). Example 4 provides a procedure for cryogenic storage and thawing of pre-loaded implant assemblies. These Examples are for illustrative purposes only and not intended to limit the scope of the invention.

EXAMPLE 1

PREPARATION OF A "DRY" ASSEMBLY

In this Example, a procedure is provided for manufacturing and testing of an implant assembly which includes a polyethylene bag and TheraCyte® implant device (Baxter Heathcare Inc., Round Lake, Ill.). FIG. 6 illustrates the procedure.

MATERIALS/EQUIPMENT:
Two 0.009" thick polyethylene sheet cut into 2"×3" sheets (Dow Chemical Company PL 1880, Midland, Mich.)
0.015" thin walled polyethylene tubing (Dow Chemical Company PE VP 1770, Midland, Mich.)
TheraCyte® ported implant device
70% and 95% ethanol filtered with 0.2 mm sterile filter
Dow Corning MDX4-4210 two-part silicone adhesive
0.040" ID×0.085" OD Silastic RX-50 Silicone Tubing (Dow Corning, Midland, Mich.)
40 kHz Branson ultrasonic welder (Branson Ultrasonics Corporation, Model No. 941 AES, Danbury, Conn.)
40 ml horn and grooved fixture (Baxter Healthcare Corporation, 40 kHz ultrasonic horn, Round Lake, Ill.)
Vertrod Thermal Impulse Heat Sealer (Vertrod Corporation, Model No. 15Mt., Brooklyn, N.Y.)
Razor blade to cut the PE sheets
Scissors
0.034"/0.028" diameter profile pins
Metal shim, 2.25" side×0.330" wide×0.004" tall

MANUFACTURING PROCEDURE:

a. SILICONE COLLAR ASSEMBLY

1. The MDX4-4210 elastomer and curing agent are mixed in a 10:1 weight ratio (total volume is about 1 to 1.5 mL) with a calibrated scale. The mixture is then placed into a syringe fitted with an 18 gauge blunt Luer adapter and centrifuged at 4° C. for 4 minutes and 1500 rpm. The centrifuged mixture is stored in 4° C. freezer.

2. The silastic tubing is cut to a 1.15" length (±0.02"). A 0.024" section of core pin is cleaned with a soap solution and excess solution is wiped off. The core pin is then inserted into the Silastic Tubing so the 0.024" profile is 0.040" from one end.

2. The silastic tubing is cut to a 1.15" length (±0.02"). A 0.024" section of core pin is cleaned with a soap solution and excess solution is wiped off. The core pin is then inserted into the Silastic Tubing so the 0.024" profile is 0.040" from one end.

3. The primed luer is inserted at the profile end amd the entire length of tubing is filled with uncured silicone. The pin is maneuvered so that an even distribution of silicone surrounds the profiled end of the pin. Air bubbles can be minimized by injecting silicone at a slow rate.

4. The syringe is removed from the silicone tube and disposed of. The entire sample is placed in an oven at 105° C. for a minimum of 10 minutes for curing purposes.

5. The sample is removed from the oven and allowed to cool. The pin is then removed from cured part and the first 0.050" of the profiled edge is removed to produce a smooth interface. The port is allowed to cure at room temperature for 24 hours prior to use.

b. DEVICE PLACEMENT AND SEALING

1. As shown in FIG. 6(*b*), a 0.028" diameter pin is inserted into the port of the device. A collar is set on the pin so the distance that the pin travels into the port is 1.18"(±0.02") for all devices. The pin does not go past the device weld edge.

2. With the Vertrod Sealer, the two PE sheets are sealed together along the three inch edges as shown in FIG. 6(*a*). The device is then placed between the two sealed PE sheets leaving approximately 0.6" of the 1.20" port length sticking out of the bag.

c. DEVICE WELDING

1. The port of the device is set into the fixture groove of the ultrasonic welder. The bag should cover at least ¼" of the bottom fixture, so that the bag and the device port may be welded in place. Weld the port two times, each side once. The recommended weld parameters are as follows: Weld Time—200 msec; Amplitude—0.9 mil at 61% Black Booster; Pressure—30 psi; Down Speed—2.1 in/sec; Hold Time—2 seconds; Energy—17–19 joules.

Figure 6A:
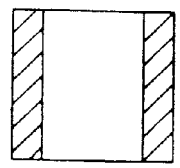
FIGS. 6(a)–(f) illustrates the preparation of an implant assembly as described in Example 1.
Figure 6B:
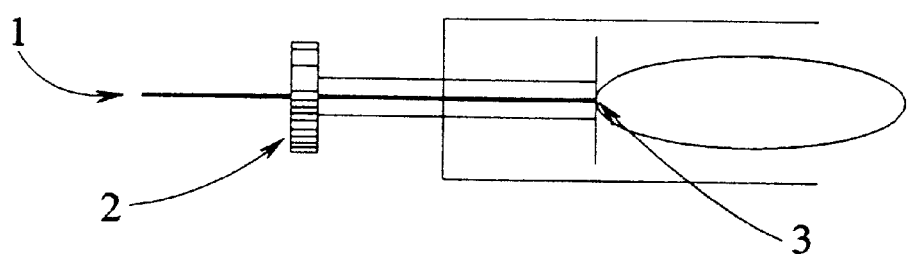
Figure 6C:
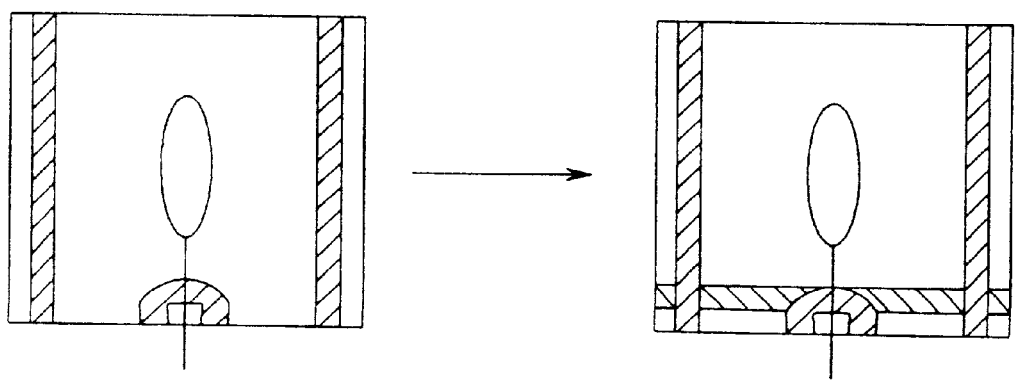

2. As shown in FIG. 6(c), the port end of the device is heat sealed with the Vertrod heat sealer. A pin and collar was used in the port so that the port will not close during sealing. The heat and dwell of the heat sealer are both set at 8. These settings should be adequate to complete the seal but not damage the material. This step will smooth out the ultrasonic weld as well as seal the end of the bag. Four to eight cycles may be necessary to complete the seal.

d. FILL PORT ASSEMBLY

Figure 6D:
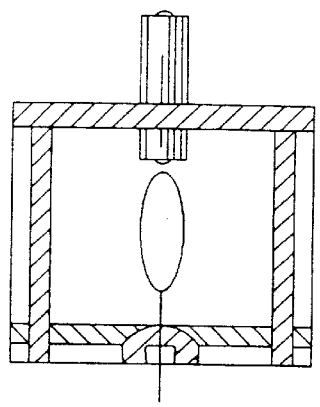

1. The 15 mm thick PE tubing (260 mil ID) is placed into the open end of the bag. A metal shim is inserted into the middle of the tubing as shown in FIG. 6(d). The heat and dwell of the heat sealer are both set at approximately 8. Four to eight cycles may be necessary to complete the seal.

e. FINAL BAG SEALING AND CUTTING

Figure 6E:
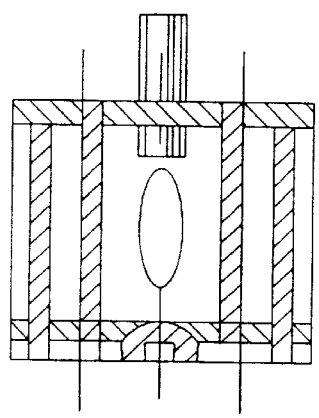

1. Once all port ends have been sealed, the bag size is reduced by head sealing each side so the final bag size is approximately 1.4" wide×3.0" long as shown in FIG. 6(e).

Figure 6F:
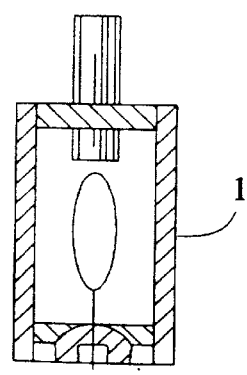
Figure 6G:
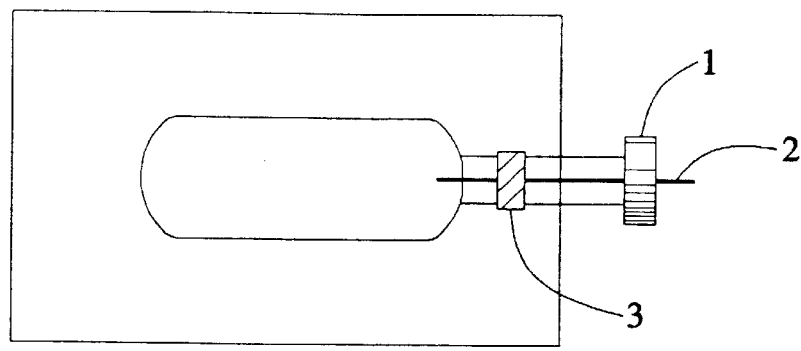
FIGS. 6(g)–(i) illustrates the preparation of the preferred embodiment using ultrasonic welding to replace heat sealing used in the process shown in FIGS. 6(a)–(f).
Figure 6H:
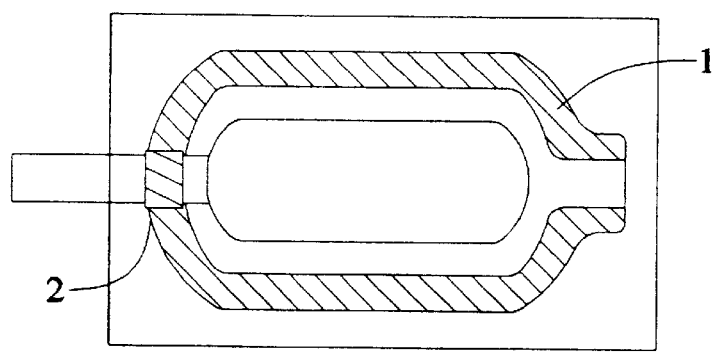
Figure 6I:
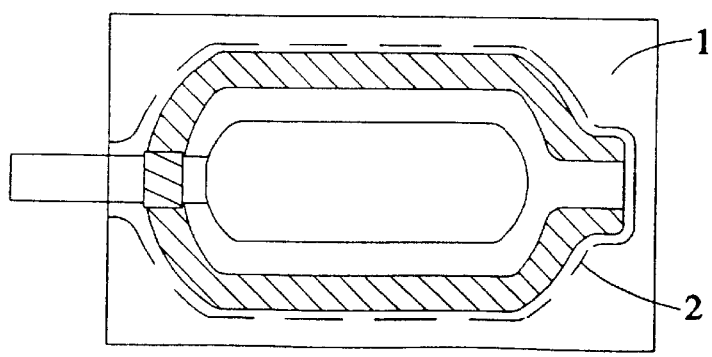

2. To ease handling, the excess polyethylene may be cut away from the outer seal edge and round bag corners before testing as shown in FIG. 6(f).

f. SILICONE COLLAR/BAG ASSEMBLY

1. The silicone collar (0.040" ID side) is manually connected to the port of the implant device in the bag. Both the silicone collar and device port are dipped in 70% ethanol.

2. The silicone collar is manually adjusted so that device port tube extends approximately 0.1 "–0.2" inside silicone collar and the length of the silicone collar/device port tube is 2.0±0.2 ". If necessary, the silicone collar (0.024" ID side) may be cut as required.

g. BAG TESTING

1. The bag is tested for leaks by wetting the device with a small amount of 0.22 $\mu$m filtered 95% ethanol. Once the device is wetted, the ethanol is poured out and the bag is filled 0.22$\mu$l filtered 70% ethanol solution. The bag is manually squeezed to prime the implant device and to create pressure on the device port seal and bag port seal. The bag is visually inspected for any small leaks or deviations in the seal.

2. Any leaks near the port may be corrected by attempting to heat seal the area again. If large leaks exist or if a leak cannot be corrected, the bagged device is removed and discarded.

3. If sterility is required, the bags may be sterilized by placing them in a bath of 0.22 $\mu$m filtered 70% ethanol to begin the sterilization process.

h. OPTIONS

Figure 7:
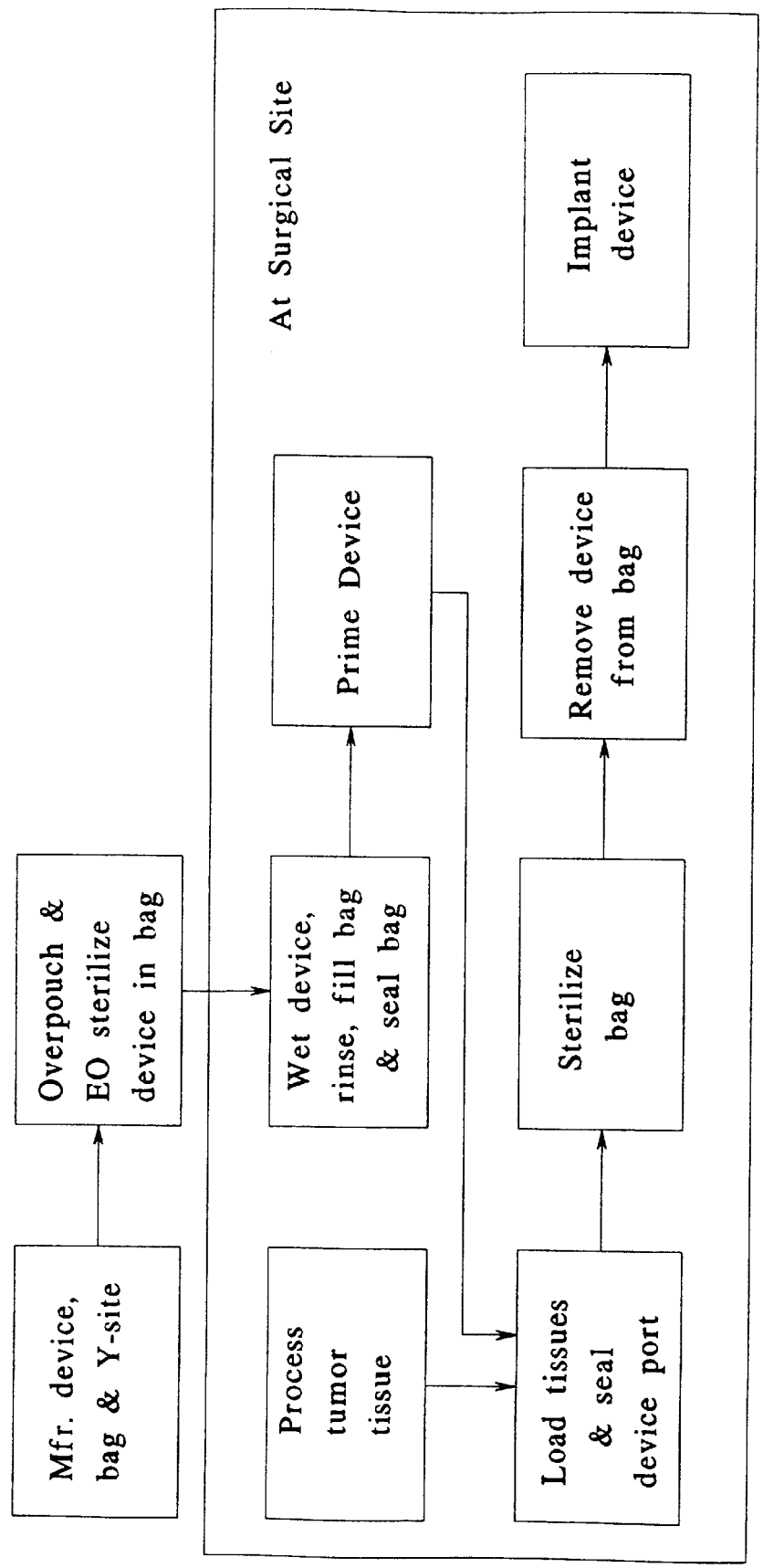
FIG. 7 is a schematic illustrating the process from manufacturing the implant assembly dry to shipping to a surgical site wherein the implant assembly is ready for wetting, priming and sealing prior to loading with cells as described in Example 1.

The implant assembly can be prepackaged in a overpouch and sterilized with ethylene oxide prior to shipping from the manufacturing plant to a surgical site as shown in FIG. 7. At the surgical site, the overpouch is removed and the sterile implant device is ready for wetting, sealing and priming prior to loading. Tumor tissue excised from a patient is processed and loaded into the implant device contained within the assembly. The exterior surface of the sealed bag container is sterilized, e.g., washed with ethanol solution, prior to removal of the device from the bag and implantation of the device into a patient.

EXAMPLE 2

PREPARATION OF A "WET" IMPLANT ASSEMBLY CONTAINING MEDIA

In this Example, a procedure is provided for the wetting, sterilization, filling, and sealing of an implant assemblies containing 4.5 $\mu$l 20 $\mu$l or 40.0 $\mu$l TheraCyte® immnunoisolation ported implant devices (Baxter Healthcare Corp., Round Lake, Ill., USA).

a. DEVICE WETTING AND STERILIZATION MATERIALS/EQUIPMENT:

Implant assembly containing a TheraCyte® ported device prepared as described in Example 1.

70% and 100% ethanol, filtered with 0.2 $\mu$m filter

Sterile saline (0.9% NaCl)

One sterile 5 cc syringe fitted with a threaded male Luer connector

Two sterile Luer stub adapters, 20 gauge

Two sterile 5 ml pipettes

One automatic pipetter

Three sterile IDL binder clips, Large Clips BC-100, Stock No. 99100 or equivalent Two sterile glass beakers Parafilm 1. A sterile 5 cc syringe fitted with a sterile Luer stub adapter is used to inject approximately 3–4 ml of filtered 100% ethanol into loading bag through bag fill port.

2. The bag fill port is either closed with binder clip or fingers. The bag is gently squeezed with fingers until device membranes appear wetted or transparent. The ethanol is drained out of the bag.

3. Steps 1 and 2 are repeated with filtered 70% ethanol. The device is gently massaged with fingers (from distal to ported end) to remove air that may be trapped in device and squeezed until ethanol drips out of device port. No air bubbles should remain in the device port tube. The 70% ethanol solution is retained in the bag.

4. The bag is then submerged into a sterile glass beaker filled with filtered 70% ethanol. The beaker with is covered with parafilm and stored under a sterile laminar hood for at least two hours to complete the sterilization process.

5. The 70% ethanol is drained out of bag and a sterile pipette containing approximately 3–4 ml of sterile saline is inserted into the bag fill port. The saline is then injected into the bag.

6. The bag fill port is then pinched closed with binder clip or with fingers. The implant device is then primed with saline by gently squeezing bag with finger until saline drips out of device port. The saline solution is retained in the bag.

7. The bag is then submerged in sterile glass beaker filled with sterile saline. The beaker is covered with parafilm and the implant assembly is soaked for at least 20 minutes.

8. Repeat steps 5–7 two times for a total of two 20-minute rinses with fresh sterile saline.

9. The wetted, sterile implant assemblies are stored in sterile saline in hood for bag filling and sealing steps.

b. BAG FILLING AND SEALING MATERIALS/EQUIPMENT:

Wetted and sterilized implant assemblies prepared as described above.

Bead sterilizer, Inotech Steri 250 or equivalent

Sterile Dulbecco's phosphate buffered saline (DPBS)

Two sterile hemostats, smooth or fine-toothed

One sterile 5 ml pipette

One automatic pipetter

One sterile tissue culture dish, 150×25 mm

PROCEDURE:

1. All materials are stored in a sterile work area within a laminer hood using aseptic techniques. The bead sterilizer is heated to a temperature of 250° C. for approximately 20 minutes. The hemostats are stored in the heated bead sterilizer for several minutes prior to use.

2. The wetted, primed sterile assembly is removed from the beaker, saline is drained out of the bag and a sterile pipette containing approximately 3–4 ml of sterile DPBS is inserted into the bag fill port so that the port tube forms an airtight seal around the pipette. The DPBS is then injected into the bag.

3. The edges of bag are gently tapped with fingers to eliminate air bubbles from DPBS and the bag is gently squeezed with fingers to bring DPBS up into bag fill port.

4. The bag fill port is clamped with the sterile heated hemostat at DPBS/air interface. Pull hemostat up, bringing end of fill port with it and leaving sealed edge behind. The end of the bag fill port is discarded and the hemostat is returned back to the bead sterilizer.

5. The bag is gently squeezed to insure that bag fill port is completed sealed. If bag fill port is not completely sealed, repeat step 4.

c. OPTIONS

Figure 8:
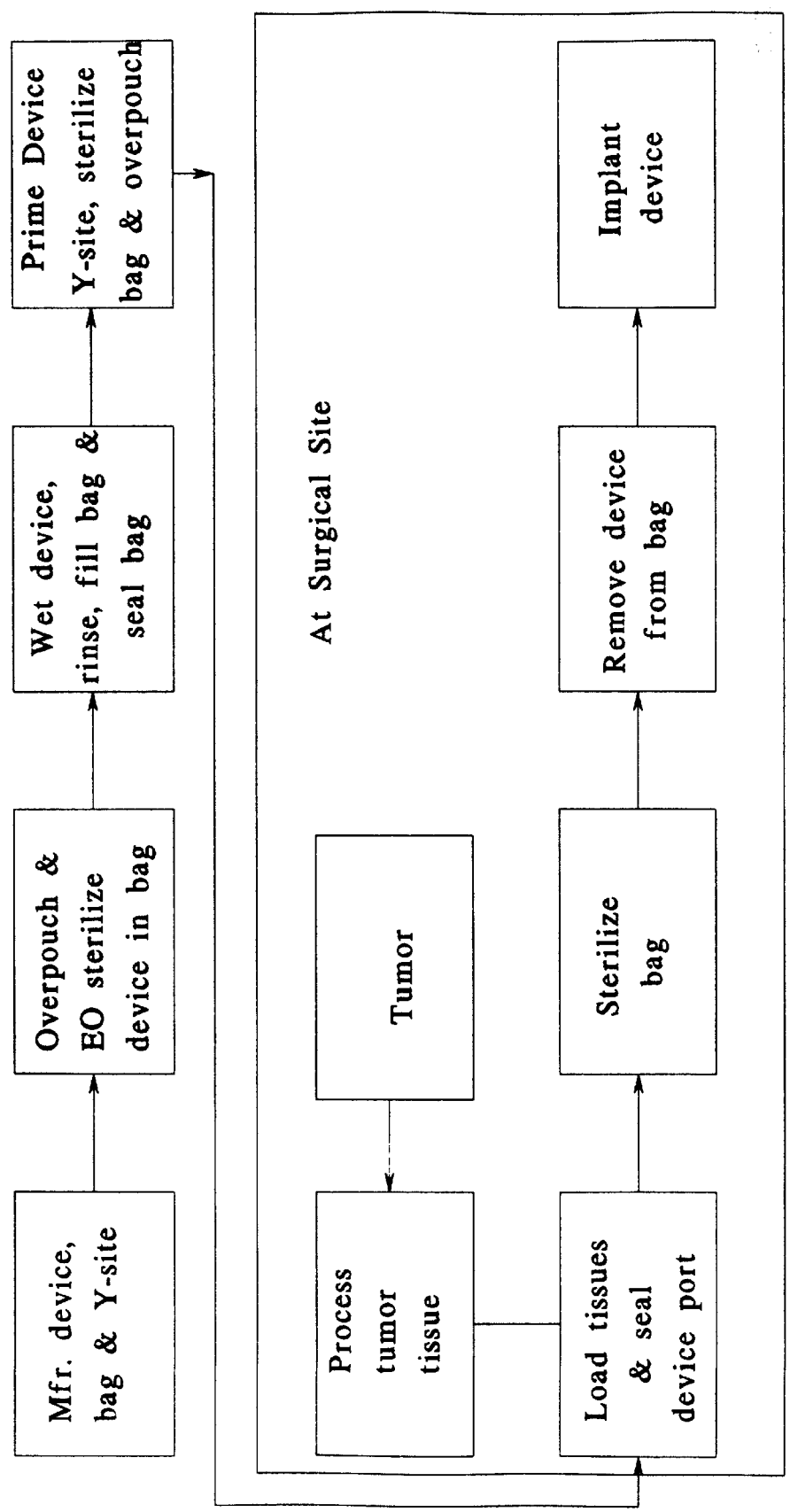
FIG. 8 is a schematic illustrating the process from manufacturing the implant assembly to shipping to a surgical site wherein the bag container has been pre-filled with sterile media and the pre-primed implant device is ready for loading with cells as described in Example 2.

A sterile implant assembly can be prepared which includes a sealed bag filled with sterile liquid, e.g., saline or growth media, and a pre-wetted and primed implant device ready for loading. The entire sterile assembly is then packaged in a overpouch prior to shipping from the manufacturing plant to a surgical site as shown in FIG. 8. At the surgical site, the overpouch is removed and the pre-wetted and primed device contained within the sterile implant assembly is ready for loading. Tumor tissue excised from a patient is processed and loaded into the implant device contained within the assembly. The exterior surface of the sealed bag is sterilized, e.g., soaked in ethanol solution, prior to removal of the device from the bag and implantation of the device into a patient.

EXAMPLE 3

PREPARATION OF A "WET" ASSEMBLY CONTAINING CELLS

In this Example, a procedure is provided for the loading of an implant assemblies prepared as described in Examples 1 and 2 which employs 4.5 $\mu$l, 20 $\mu$l and 40.0 $\mu$l TheraCyte® ported implant devices with cells or tissue for experimental use. A procedure is also provided for resterilization of the bag component of the implant assembly prior to removal of the loaded implant device from the assembly and implantation into a patient.

The following cell concentration of MSU 1.2 cells and loading volumes are used: For 40$\mu$l devices: approximately $2.0 \times 10^7$ cells in a final volume of 40 $\mu$l are loaded into the 40 $\mu$l device; For 20 $\mu$l device: approximately $1.0 \times 10^7$ cells in a final volume of 20 $\mu$l are loaded into the 20 $\mu$l device. For 4.5 $\mu$l devices: approximately $1.0 \times 10^6$ cells in a final volume of 5 $\mu$l are loaded into the 4.5 $\mu$l device. If desired, less dense cell concentrations may be used. For example, $2.0 \times 10^7$ cells in a final volume of 60 $\mu$l may be used for the 40 $\mu$l device, or $1.0 \times 10^7$ cells in a final volume of 30 $\mu$l may be used for the 20 $\mu$l device.

a. MATERIAL PREPARATION

1. The following materials are placed into sterilization pouches as follows:

Pouch #1: One glass test tube (or equivalent) containing: one Hamilton syringe barrel (Teflon® tip down); one Hamilton syringe plunger; one blunted 22 gauge Hamilton needle.

Pouch #2: One glass petri dish (or equivalent) containing: Silicone collars, profiled (0.080" OD×0.040" ID, 0.080" OD×0.024" ID (n=1 per device).

Pouch #3: One atraumatic forceps.

Pouch #4: One glass beaker.

Pouch #5: One atraumatic forcep; one scissor; and one scalpel handle.

Pouch #6: Gauze sponges (n=1 per device)

2. Pouch #1 is autoclaved using an isothermal cycle, no greater than 95° C., for a period no longer than 15 minutes.

3. Pouches #2, #3, #4, #5, and #6 are autoclaved using gravity cycle, no greater than 121° C., for a period no longer than 30 minutes.

b. DEVICE LOADING PROCEDURE

MATERIALS/EQUIPMENT:

Sterile implant assemblies prepared as described in Examples 1 and 2 containing filled and sealed loading bags.

Silastic Medical Adhesive Silicone Type A, sterile.
One sterile 3 cc syringe with threaded male Luer connector.
One sterile sharp 20 gauge needle.
One sterile scalpel blade, size 10.
One sterile tissue culture dish, 150×25 mm.
Gauze sponges, sterile (optional)
Sterile growth media or equivalent
70% ethanol filtered with a 0.2 $\mu$m filter.
Sterile Pouches #1–3 i. LOADING PREPARATION

1. A sterile work area is created within a laminar flow hood and all loading materials is placed in the work area using aseptic technique.

2. The 3 cc syringe is filled with the silicone adhesive by removing the plunger and docking adhesive tube to proximal end of the syringe. Approximately 1.5 cc of adhesive is dispensed into syringe barrel.

4. The 3 cc syringe plunger is reconnected and all air is expelled from the syringe by slowly inserting the plunger. The syringe is visually inspected to make sure adhesive is free of air bubbles.

5. The 20 gauge needle is connected to the syringe and is primed with adhesive by pushing approximately 0.5 cc adhesive through needle. Excess adhesive is wiped off with sterile gauze. Adhesive containing syringe will be referred to as the "sealing syringe." Note that the syringe is filled with medical adhesive within 15 minutes of initial use. The adhesive may remain within syringe without curing for at least one hour.

6. The Hamilton syringe is assembled by wetting Teflon® plunger and inserting into glass barrel. Damage to Teflon® plunger tip may occur if the plunger is inserted into the syringe barrel while dry. The syringe needle and Teflon® O-ring washer is wetted by dipping in sterile saline or media and connecting to distal end of glass barrel.

7. The Hamilton syringe and needle is primed by using the plunger to repeatedly aspirate and expel media from needle until no air bubbles are visually detected in glass syringe barrel.

ii. LOADING PROCEDURE

1. In a sterile environment, the implant assembly is removed from a sterile tissue culture dish.

2. If silicone collar is not connected to the implant device, silicone collar (0.040" ID side) may be connected manually to the device port tube, being careful not to touch end of port tube with fingers. The silicone collar is adjusted so that device port tube extends approximately 0.1–0.2" inside silicone collar.

3. The silicone collar is primed with DPBS by gently squeezing bag until DPBS drips out of silicone collar and no air bubbles are no longer visible in the device port tube and silicone collar.

4. The length of silicone collar/device port tube is compared to the length of Hamilton needle. If Hamilton needle can travel more than half way into welded section of device port tube, the silicone collar on device port tube may be repositioned or cut (0.024" ID side) as required.

5. Using a sterile Hamilton syringe fitted with a sterile blunted 22 gauge needle, the volumes of cell suspension and media amounts drawn up into the syringe are listed below. To maintain consistent cell suspension, vortex or mix cells before loading into syringe.

a) For a 40 $\mu$l device, a 100 $\mu$l syringe is used to draw up 10 $\mu$l of media followed by 40 $\mu$l of cell suspension; total syringe volume is 50 $\mu$l.

b) For a 20 $\mu$l device, a 25 ml syringe is used to draw up 5 $\mu$l of media followed by 20 $\mu$l of cell suspension; total syringe volume is 25 $\mu$l.

c) For a 4.5 $\mu$l device, a 25 $\mu$l syringe is used to draw up 5 $\mu$l of media followed by 5 $\mu$l of cell suspension; total syringe volume is 10 $\mu$l.

6. The Hamilton syringe needle is inserted into the silicone collar, through device port, until syringe hub contacts silicone collar. Hamilton needle should not travel more than half way into welded section of port tube. The needle tip should not enter into the device or touch the device membranes within the lumen. If needle tip does enter device, the device should be discarded.

7. The contents of Hamilton syringe is then injected into the implant device. Syringe and loading bag may be lifted into the air to aid in handling. The Hamilton syringe needle is slowing withdrawn until the tip of needle is near or within 0.024" ID portion of silicone collar. Holding onto the 0.024" ID portion of silicone collar may aid in withdrawal. The syringe is left connected to silicone collar. Note that some cells may travel up device port when Hamilton needle is withdrawn. The device port tube and silicone collar is then visually inspected for air bubbles within the media.

Figure 9:
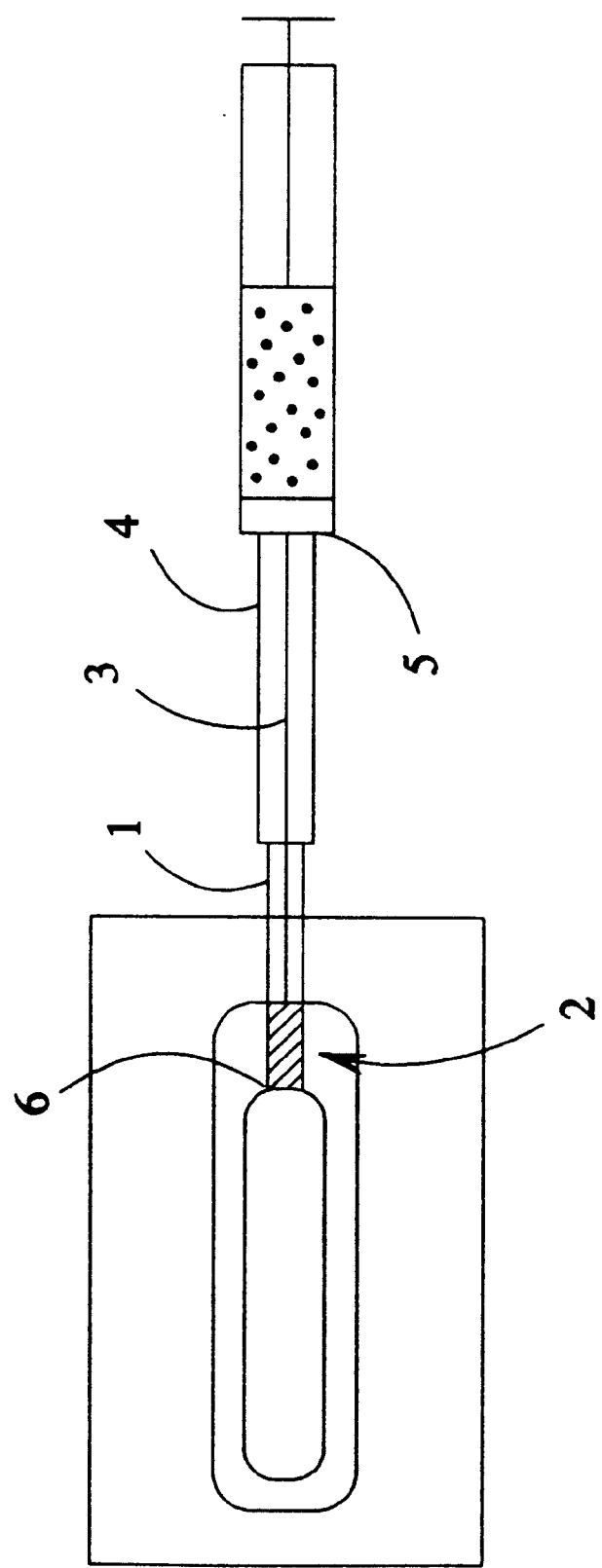
FIG. 9 illustrates the process of loading cells into a prewetted, primed implant device contained in the implant assembly.

8. If no air bubbles are seen in the media, the sealing syringe needle is inserted into the device port tube by piercing the silicone collar as shown in FIG. 9. The needle tip should be just inside the device port. Forceps may be used to hold silicone collar in place.

9. If air bubbles are seen in the media, the device port tube is pierced with the sealing syringe needle at media/air interface. Be sure needle opening is completely within port tube. Forceps may be used to hold device port tube in place.

10. Silicone adhesive is then slowly injected into the device port tube until adhesive reaches inner lumen of device. The sealing syringe is left in place. For 40 $\mu$l devices, some resistance to silicone flow upon reaching device inner lumen should be noted. The silicone adhesive volume is approximately 0.05 cc.

11. With Hamilton syringe and sealing syringe still connected to device, a sterile scalpel blade is used to cut device port tube at approximately 0.1–0.2" past the edge of bag. The device port tube is visually inspected for silicone extrusion. If silicone extrusion is observed, device should be discarded.

12. The bag is stored in a covered sterile tissue culture dish for resterilization prior to implantation.

c. BAG RE-STERILIZATION
    MATERIALS/EQUIPMENT:
Implant assemblies containing loaded implanted devices and sealed bags prepared as described above.
70% ethanol solution filtered with 0.22 $\mu$m filter
Pouch #4, sterile
Parafilm
    PROCEDURE
1. In a sterile environment, the sealed bags are placed into a sterile glass beaker filled with filtered 70% ethanol and covered with paraflim. The bags are soaked in the ethanol solution for 5–10 minutes.

d. DEVICE REMOVAL FROM BAGS
    MATERIALS/EQUIPMENT:
Sterilized implant assembly containing a loaded implant device and sealed, filled bag.
One sterile scalpel blade, size 10.
One sterile tissue culture dish, 150×25 mm.
Pouches #5 and #6, sterile
    i. DEVICE REMOVAL PROCEDURE:
1. A sterile work area is created within hood and all materials are placed into the work area using aseptic technique. The lid of the tissue culture dish is removed and placed lid inside up.

2. A piece of sterile gauze is inserted on inside lid of tissue culture dish. The sterile assembly is removed from the beaker and the outside surface is wiped down with the gauze.

3. The sterile scissors is then used to cut off port end of bag. The DPBS media is drained out of bag into waste container and the side edges of the bag are then cut off.

4. The two sides of bag are folded back so that device protrudes from inside bag. Be care full not to allow any fluid which may remain on outside of bag to come into contact with device. The device is laid down on the sterile gauze in tissue culture dish lid with the back sides of bag held back.

5. The sterile atraumatic forceps is used to hold distal end of device, touching device only along the seal edge. A sterile scalpel blade is used to cut device port tube flush with edge of device.

6. The device is lifted with forceps, touching device only by the port tube or along the seal edge and the device port tube is visually inspected for silicone extrusion. If silicone extrusion is observed, device is discarded.

7. The device is then placed in an individual container filled with growth media and incubated at 37 ° C., 5% $CO_2$ until implantation.

e. OPTIONS:
A sterile implant assembly can be prepared which includes a sealed bag pre-filled with sterile liquid, e.g., saline, growth media, or cryopreservation media, and an implant device pre-loaded with allograft cells. The entire sterile assembly is then packaged in a overpouch at the manufacturing facility and either shipped to the surgical site for immediate implantation or cryopreserved for future use. In the latter case, the frozen implant device contained in the assembly can be shipped to the surgical site, thawed and removed from the assembly for implantation as shown in FIG. 10.

EXAMPLE 4

IMPLANT ASSEMBLY CRYOPRESERVATION

In this example, three sterile wet implant assemblies were constructed as described in Example 3 and containing DMEM growth media having 8% DMSO. MCA-38 cells (2.0×10$^7$) were added into the assembly and the port was sealed as described in Example 3. The implant assemblies was then immediately immersed and stored in liquid nitrogen for three days. One implant assembly was quickly thawed in a 37° C. water bath, the device quickly cut out of the bag and placed in a 100 mm petri dish containing MCA-38 media. The device was then cut open using a scalpel blade and the dish (with the device) was stored in an incubator at 37° C. under a 5% $CO_2$ atmosphere over night. Approximately 43% of the cells removed from the device remained viable based on the conventional trypan blue stain cell counting technique.

After approximately two months of storage in liquid nitrogen, the remaining two implant assemblies were quickly thawed and the devices implanted immediately into the epididymal fat pad of an anesthetized athymic rat. A control athymic rat received a fresh (never frozen) implant device containing MCA 38 cells. After three weeks, the animals were sacrificed and the devices were explanted and histogically inspected. No visible abnormalities were observed in either rat and no external tumors were present in any of the devices. Histology of the devices demonstrated no differences between devices containing fresh or frozen cells.

While the present invention has been described in terms of specific methods and devices, it will be understood that variations and modifications will occur to those skilled in the art upon consideration of the present invention. Numerous modifications and variations in the invention as described in the above illustrative examples are expected to occur to those skilled in the art and consequently only such limitations as appear in the appended claims are to be placed thereon. Accordingly, it is intended in the appended claims to cover all such equivalent variations which come within the scope of the invention as claimed.

What is claimed is:

1. An implant assembly comprising:
   (a) an implant device comprising porous walls defining a first chamber and having an elongated port means providing access to the first chamber; and
   (b) a removable container defining a second chamber for holding the implant device, the container having a means for admitting liquids into the second chamber, wherein the elongated port means extends from the first chamber through the container and the exterior of the port means forms a seal with the container.

2. The assembly according to claim 1 wherein the elongated port means is in communication with multiple access means for providing multiple access to the elongated port means.

3. The assembly according to claim 2 wherein the second chamber contains liquid and the means for admitting liquid and the elongated port means are closed.

4. The assembly according to claim 2 wherein the first chamber contains materials to be implanted and, the second chamber contains liquid and the interior of the elongated port is sealed.

5. The assembly according to claim 4 wherein the first chamber contains cells or tissue to be implanted.

6. The assembly according to claims 1,2,3,4 or 5 wherein the implantation assembly is sealed in a sterile pouch.

7. The assembly according to claim 2 wherein the multiple access means includes first and second access means for accessing the multiple access means, the first access means is fitted with a device for delivering materials to the first chamber of the implant device through the elongated port and the second access means is fitted with a device containing a sealant for delivering sealant to plug the elongated port after material is delivered to the first chamber.

8. The assembly according to claim 7, wherein the sealant contains a colorant.

9. An implant assembly comprising:
   (a) an implant device comprising porous walls defining a first chamber and having an elongated port means providing access to the first chamber;
   (b) a removable container defining a second chamber for holding the implant device, the container having a means for admitting liquids into the second chamber, wherein the elongated port means extends from the first chamber through the container and the exterior of the port means forms a seal with the container; and
   (c) a liquid contained in the second chamber.

10. The assembly according to claim 9 wherein the elongated port means is in communication with multiple access means.

11. The assembly according to claim 10 wherein the means for admitting liquid and the multiple access means are closed.

12. The assembly according to claim 10 wherein the first chamber contains materials to be implanted and the interior of the elongated port is sealed.

13. The assembly according to claim 12 wherein the first chamber contains cells or tissue to be implanted.

14. The assembly according to claims 9, 10, 11, 12 or 13 wherein the implantation assembly is sealed in a sterile pouch.

15. The assembly according to claim 10 wherein the multiple access means includes first and second access means for accessing the multiple access means, the first access means is fitted with a device for delivering materials to the first chamber of the implant device through the elongated port and the second access means is fitted with a device containing a sealant for delivering sealant to plug the elongated port after material is delivered to the first chamber.

16. The assembly according to claim 15, wherein the sealant contains a colorant.

17. An implant assembly comprising:
   (a) an implant device comprising porous walls defining a first chamber and having an elongated port means providing access to the first chamber;
   (b) cells or tissue contained in the first chamber;
   (c) a removable container defining a second chamber for holding the implant device, the container having a means for admitting liquids into the second chamber, wherein the elongated port means extends from the first chamber through the container and the exterior of the port means forms a seal with the container; and
   (d) a liquid contained in the second chamber for maintaining the cells or tissue.

18. The assembly according to claim 17 wherein the elongated port means is in communication with multiple access means for providing multiple access to the elongated port means.

19. The assembly according to claim 18 wherein the first chamber contains liquid and the means for admitting liquid and the elongated port means are closed.

20. The assembly according to claim 18 wherein the first chamber contains materials to be implanted and, the second chamber contains liquid and the interior of the elongated port is sealed.

21. The assembly according to claim 20 wherein the first chamber contains cells or tissue to be implanted.

22. The assembly according to claim 17 wherein the liquid is a cryopreservation medium.

23. The assembly according to claims 17, 18, 19, 20, 21, or 22 wherein the implantation assembly is sealed in a sterile pouch.

24. The assembly according to claim 18 wherein the multiple access means includes first and second access means for accessing the multiple access means, the first access means is fitted with a device for delivering materials to the first chamber of the implant device through the elongated port and the second access means is fitted with a device containing a sealant for delivering sealant to plug the elongated port after material is delivered to the first chamber.

25. The assembly according to claim 24, wherein the sealant contains a colorant.

* * * * *